United States Patent
Elmaanaoui

(10) Patent No.: US 10,234,676 B1
(45) Date of Patent: Mar. 19, 2019

(54) OPTICAL PROBES WITH REFLECTING COMPONENTS FOR ASTIGMATISM CORRECTION

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

(*) Notice: Subject to any disclaimer, the term of this patent is extended or adjusted under 35 U.S.C. 154(b) by 0 days.

(21) Appl. No.: 15/879,306

(22) Filed: Jan. 24, 2018

(51) Int. Cl.
| | |
|---|---|
| G02B 23/24 | (2006.01) |
| G02B 23/02 | (2006.01) |
| G02B 27/00 | (2006.01) |
| G02B 6/26 | (2006.01) |
| G02B 6/32 | (2006.01) |
| A61B 5/02 | (2006.01) |
| G01B 9/02 | (2006.01) |
| A61B 5/00 | (2006.01) |
| A61B 1/05 | (2006.01) |
| G02B 23/26 | (2006.01) |

(52) U.S. Cl.
CPC ............ *G02B 23/2423* (2013.01); *A61B 1/05* (2013.01); *A61B 5/0066* (2013.01); *A61B 5/02007* (2013.01); *G01B 9/0205* (2013.01); *G02B 6/262* (2013.01); *G02B 6/32* (2013.01); *G02B 23/02* (2013.01); *G02B 23/2446* (2013.01); *G02B 23/26* (2013.01); *G02B 27/0025* (2013.01)

(58) Field of Classification Search
CPC ...... G02B 6/262; G02B 6/32; G02B 23/2423; G02B 23/02; G02B 23/2446; G02B 23/26; G02B 27/0025; G01B 9/0205; A61B 1/05; A61B 5/0066; A61B 5/02007

USPC .......................................................... 385/35
See application file for complete search history.

(56) References Cited

U.S. PATENT DOCUMENTS

| | | | |
|---|---|---|---|
| 6,433,937 B1 | 8/2002 | Konno | |
| 6,445,939 B1 | 9/2002 | Swanson | |
| 6,501,878 B2 | 12/2002 | Hughes | |
| 6,564,087 B1 | 5/2003 | Pitris et al. | |
| 6,801,375 B2 | 10/2004 | Hayashide | |
| 6,954,296 B2 | 10/2005 | Takakubo | |

(Continued)

FOREIGN PATENT DOCUMENTS

| | | |
|---|---|---|
| JP | H04-60608 A | 2/1992 |
| WO | 2015116939 A1 | 8/2015 |
| WO | 2016077252 A1 | 5/2016 |

OTHER PUBLICATIONS

Yu-Kuan Lu et al., Asymmetric elliptic-cone-shaped microlens for efficient coupling to high-power laser diodes, Optics Express, vol. 15, No. 4, Feb. 19, 2007.

(Continued)

*Primary Examiner* — Jerry M Blevins
(74) *Attorney, Agent, or Firm* — Canon U.S.A., Inc. I.P. Division

(57) ABSTRACT

Some devices comprise a first light-guiding component, a second light-guiding component, a lens, an optical-correction component that has a reflecting surface that faces the lens, and a sheath, which causes astigmatism. The reflecting surface has an optical power on a first axis of two orthogonal axes, the optical power on the first axis compensates for the astigmatism, and the reflecting surface has a negligible optical power on a second axis of the two orthogonal axes. Also, the reflecting surface is configured to reflect light from the lens and redirect the reflected light through the sheath.

26 Claims, 10 Drawing Sheets

(56) References Cited

U.S. PATENT DOCUMENTS

| | | | |
|---|---|---|---|
| 7,366,376 | B2 | 4/2008 | Shishkov |
| 7,457,044 | B2 | 11/2008 | Ohzawa |
| 7,492,987 | B2 | 2/2009 | Yeik et al. |
| 7,680,378 | B2 | 3/2010 | Alphonse |
| 7,813,609 | B2 | 10/2010 | Petersen |
| 8,180,134 | B2 | 5/2012 | Wang |
| RE43,875 | E | 12/2012 | Shishkov |
| 8,425,500 | B2 | 4/2013 | Hanley et al. |
| 8,515,221 | B2 | 8/2013 | Flanders |
| 8,582,934 | B2 | 11/2013 | Adler |
| 8,781,287 | B2 | 7/2014 | Flanders |
| 8,971,679 | B2 | 3/2015 | Ho |
| RE45,512 | E | 5/2015 | Tearney |
| 9,036,966 | B2 | 5/2015 | Bhagavatula |
| 9,069,122 | B2 | 6/2015 | Takeuchi |
| 9,087,368 | B2 | 7/2015 | Tearney |
| 9,164,272 | B2 | 10/2015 | Maillard |
| 9,318,810 | B2* | 4/2016 | Zelenski ............... H01Q 19/193 |
| 9,488,782 | B2 | 11/2016 | Griffin |
| 9,662,173 | B1 | 5/2017 | Griffin |
| 2005/0165315 | A1 | 7/2005 | Zuluaga |
| 2006/0067620 | A1 | 3/2006 | Shishkov |
| 2007/0233396 | A1 | 10/2007 | Tearney |
| 2008/0013960 | A1 | 1/2008 | Tearney |
| 2009/0244545 | A1 | 10/2009 | Toida |
| 2009/0306477 | A1 | 12/2009 | Togino |
| 2011/0137124 | A1 | 6/2011 | Milner |
| 2011/0141759 | A1 | 6/2011 | Smith |
| 2012/0101374 | A1 | 4/2012 | Tearney et al. |
| 2014/0288417 | A1 | 9/2014 | Schmidtlin et al. |
| 2015/0378105 | A1 | 12/2015 | Godbout et al. |
| 2016/0274345 | A1* | 9/2016 | Ueno ............... G02B 21/0076 |
| 2016/0299170 | A1 | 10/2016 | Ito et al. |
| 2017/0168232 | A1 | 6/2017 | Tearney et al. |
| 2017/0235126 | A1 | 8/2017 | DiDomenico |
| 2018/0070932 | A1* | 3/2018 | Tearney ............... A61B 10/04 |

OTHER PUBLICATIONS

SPIE, Gradient Index Lens, Optipedia, Internet Archive Wayback Machine, May 16, 2016, downloaded from http://web.archive.org/web/20160516035942/http://spie.org/publications/tt48_55_gradient_index_lens.

Zhen Qiu et al., New Endoscopic Imaging Technology Based on MEMS Sensors and Actuators, Micromachines 2017, Jul. 2017.

Tianshi Wang et al., Numerical Analysis of Astigmatism Correction in Gradient Refractive Index Lens Based Optical Coherence Tomography Catheters, Applied Optics, 51(21):5244-5252, Jul. 20, 2012.

Woonggyu Jung et al., Numerical Analysis of Gradient Index Lens-Based Optical Coherence Tomography Imaging Probes, Journal of Biomedical Optics, vol. 15(6), Nov. 2010.

D. Yelin et al., Three-dimensional miniature endoscopy, Nature, Oct. 19, 2006, pp. 765—vol. 441.

* cited by examiner

OPTICAL PROBES WITH REFLECTING COMPONENTS FOR ASTIGMATISM CORRECTION

BACKGROUND

This application generally concerns optical probes.

An optical-imaging catheter or endoscope's optical system is usually fragile and therefore is often protected by a sheath. Astigmatism is created in the optical system by the shape of the sheath. Astigmatism causes the foci of the beams of light in two orthogonal directions to converge at different distances with different beam sizes or to diverge in one direction while converging in another direction. This astigmatism reduces the image quality of the optical system.

SUMMARY

Some embodiments of a device comprise a first light-guiding component, a second light-guiding component, a lens, an optical-correction component that has a reflecting surface that faces the lens, and a sheath. Also, the sheath causes an astigmatism, the reflecting surface has an optical power on a first axis of two orthogonal axes, the optical power on the first axis compensates for the astigmatism, the reflecting surface has a negligible optical power on a second axis of the two orthogonal axes, the reflecting surface is configured to reflect light from the lens and redirect the reflected light through the sheath, and the optical-correction component does not directly contact the lens.

Some embodiments of a device comprise a first light-guiding component, a second light-guiding component, an optical-focusing component, and an optical-correction component that has a reflecting surface that faces the optical-focusing component. Also, the reflecting surface has an optical power and is configured to reflect light from the optical-focusing component and redirect the reflected light.

Some embodiments of a device comprise a first light-guiding component, a second light-guiding component, a lens, a protector that surrounds at least part of the lens and that includes a window, and an optical-correction component that has a reflecting surface that faces the lens. Also, the reflecting surface has an optical power and is configured to reflect light from the lens and redirect the reflected light through the window of the protector.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Some optical-imaging devices (e.g., endoscopes) are configured to capture images from inside a subject, such as a human patient. These optical-imaging devices may include an optical probe, and the optical probe may include both a lens and a mirror at a distal tip. Also, one or more optical fibers in the optical probe can be used to navigate the optical probe to an object (e.g., organs, tissues), deliver light to the object, and detect light that is reflected by the object. Furthermore, an optical-imaging device may include a sheath that encloses the optical probe.

For example, an optical probe that is configured for optical coherence tomography (OCT) can capture depth-resolved images of the blood vessels in the surface of an object (e.g., an organ). As a beam of light from the optical probe is rotated across the surface, the optical probe can obtain cross-sectional images of the blood vessels in the surface. In order to obtain three-dimensional data, the optical probe can be translated longitudinally during the rotation to obtain images from a helical-scanning pattern. This helical scanning may be performed by pulling the tip of the optical probe back towards a proximal end while the optical probe is being rotated or by pushing the tip of the optical probe towards a distal end while the optical probe is being rotated.

The sheath may be transparent or mostly transparent so that the beam of light can travel through the sheath. The sheath has an optical power, although the optical power of the sheath is not very strong when the medium inside and the medium outside the sheath are the same (e.g., the media inside and outside the sheath are both air, the media inside and outside the sheath are both the same contrast agent). However, if the media are different, then the sheath has a stronger optical power. For example, if the medium inside the sheath is air and the medium outside the sheath is a contrast agent, then the sheath will have a negative optical power in the sagittal direction. Additionally, the smaller the diameter of the sheath, the stronger the optical power of the sheath, and the greater the astigmatism caused by the sheath.

Figure 1:
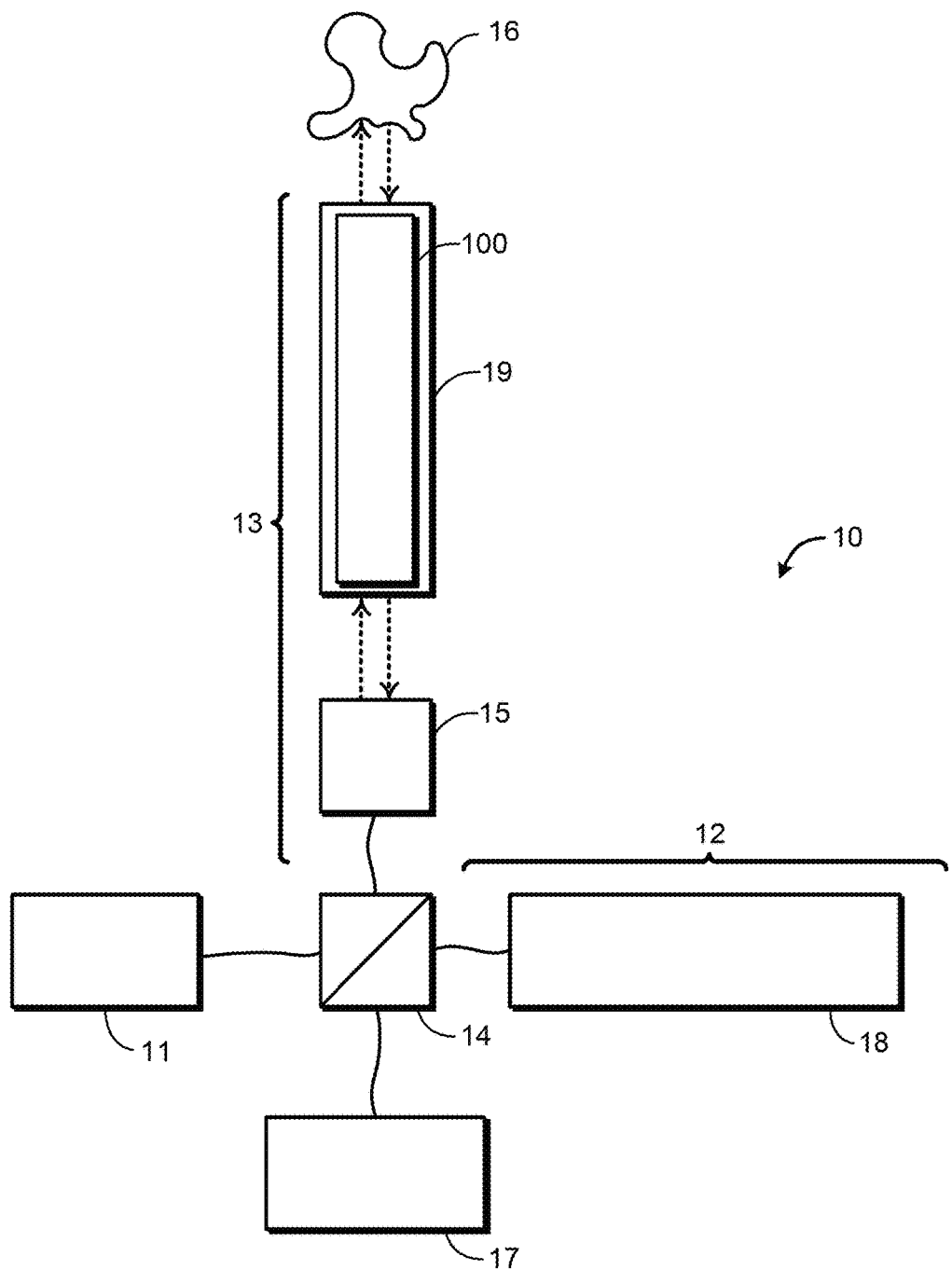
FIG. 1 illustrates an example embodiment of an optical-coherence-tomography (OCT) system.

FIG. 1 illustrates an example embodiment of an OCT system. The OCT system 10 includes a light source 11, a reference arm 12, a sample arm 13, a beam splitter 14, and one or more detectors 17. The light source 11 emits light, and the light source 11 may be, for example, a broad-band light source with a short coherence length, a superluminescent light-emitting diode (SLED), a tunable light source, or a white-light source. The beam splitter 14 splits the light, directs some of the light to the reference arm 12, and directs some of the light to the sample arm 13. Also, some embodiments of the OCT system 10 use one or more circulators to split the light and use one or more beam couplers to recombine the light.

The sample arm 13 includes a patient-interface unit 15 and an optical-imaging device 19. The optical-imaging device 19 includes an optical probe 100, which directs a beam of light to a sample 16 and detects light that is reflected from or scattered by the sample 16. The optical probe 100 then transmits this detected light back to the beam splitter 14.

The reference arm 12 includes an optical delay line 18. The optical delay line 18 includes a mirror, and light that travels through the optical delay line 18 is reflected off the mirror and then travels back to the beam splitter 14.

The beams from the sample arm 13 and the reference arm 12 are recombined by the beam splitter 14, which generates a recombined beam that has an interference pattern. The recombined beam is detected by the one or more detectors 17 (e.g., photodiodes, photomultiplier tubes, a linear CCD array, an image sensor, a CCD array, a CMOS array).

Figure 2:
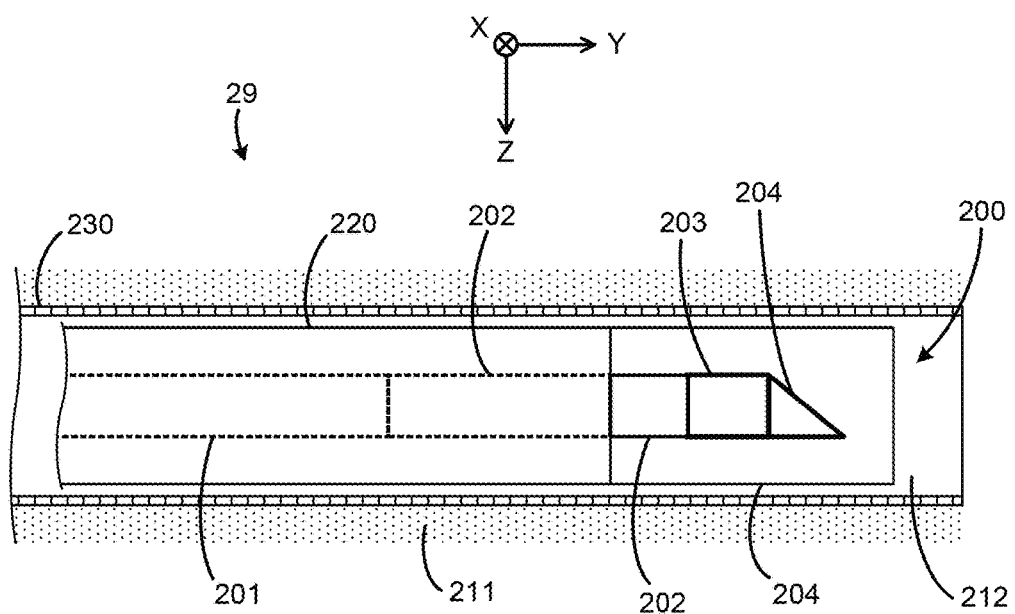
FIG. 2 illustrates a partially-cutaway view of an example embodiment of an optical-imaging device that includes an optical probe, a drive cable, and a sheath.

FIG. 2 illustrates a partially-cutaway view of an example embodiment of an optical-imaging device 29 (e.g., an optical-imaging catheter, an endoscope) that includes an optical probe 200, a drive cable 220, a protector 204, and a sheath 230. The optical probe 200 includes a first light-guiding component 201, which is a waveguide (e.g., a single-mode optical fiber, a multimode optical fiber, a double-clad optical fiber); a second light-guiding component 202, which is also a waveguide (e.g., a glass rod, a glass spacer, a large-core multimode fiber); an optical-focusing component 203 (e.g., a gradient-index (GRIN) lens, a ball lens, a half-ball lens, a graded-index (GI) fiber); and a light-reflecting component 204 (e.g., a prism). Also, the sheath 230 contains the protector 204, which surrounds part of the optical probe 200, and contains an inner medium 212 (e.g., air, a contrast agent), which is the medium inside the sheath 230. The sheath 230 is surrounded by an outer medium 211 (e.g., air, a contrast agent), which is the medium outside the sheath 230. The sheath 230 may be mostly transparent or may include a transparent or mostly-transparent window. Furthermore, the sheath 230 may introduce a negative optical power along a first axis (the x axis in FIG. 2) and introduce almost no optical power along a second axis (the y axis in FIG. 2).

The drive cable 220, the protector 204, and the optical probe 200 are fixed relative to each other, and the optical probe 200 can freely spin inside of the sheath 230. The drive cable 220 delivers torque from its proximal end to its distal end in order to spin the distal end, which is attached to the optical probe 200. Spinning the optical probe 200 permits the optical probe to capture a 360° view.

Without correction, the optical-imaging device 29 may suffer from astigmatism caused by the sheath 230. The sheath's inner and outer surfaces are mostly flat in the tangential direction and thus have almost no influence on the optical power of the optical-imaging device 29. The sheath's inner and outer surfaces are curved in the sagittal direction. The inner surface has a negative optical power when air is the inner medium 212 because light travels from the air to the concave inner surface of the sheath 230. The outer surface has a positive optical power when air is the outer medium 211 because light travels from the concave outer surface of the sheath 230 to the air. However, the optical power at the outer surface is not as strong as the optical power at the inner surface because the radius of the curvature of the outer surface is larger than the radius of the curvature of the inner surface. Also, the sheath's material typically has an index of refraction (IOR) in the rage of 1.3 to 1.6, which causes the optical power of the outer sheath to be weaker or slightly negative when the outer medium 211 is a contrast agent and not air. Some contrast agents have an IOR in the range of 1.43 to 1.47.

Figure 3A:
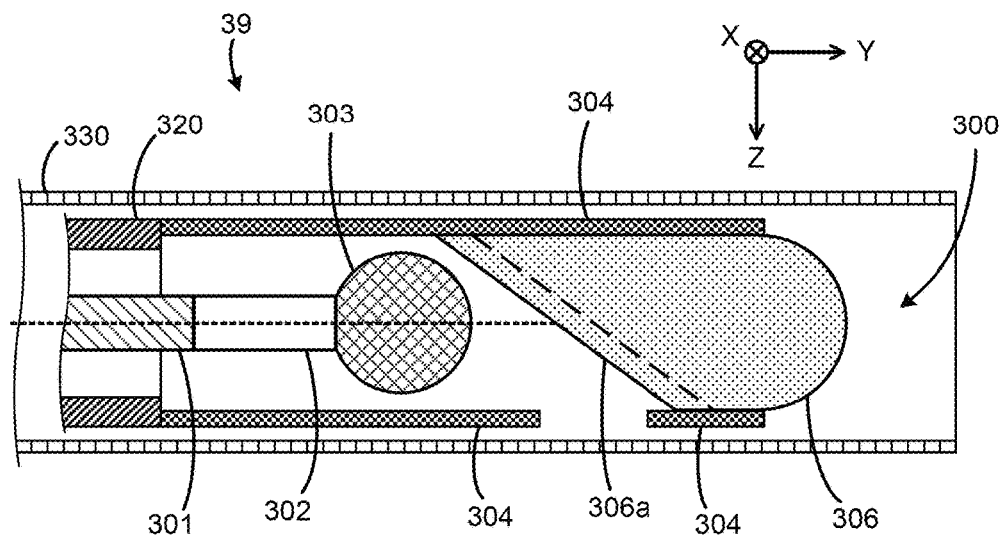
FIG. 3A illustrates a partially-cutaway view of an example embodiment of an optical-imaging device that includes an optical probe, a drive cable, and a sheath.

FIG. 3A illustrates a partially-cutaway view of an example embodiment of an optical-imaging device 39 that includes an optical probe 300, a drive cable 320, and a sheath 330. The optical probe 300 includes a first light-guiding component 301 (e.g., an optical fiber), a second light-guiding component 302 (e.g., a glass-rod spacer), an optical-focusing component 303 (e.g., lens), a protector 304, and an astigmatism-correction and beam-steering component (ACBS) 306.

The first light-guiding component 301 and the second light-guiding component 302 are configured to deliver one or more beams of light to the distal tip of the optical probe 300. The first light-guiding component 301 may be, for example, a double-clad fiber, a multimode fiber, a polarization-maintaining fiber, or a single-mode fiber. The second light-guiding component 302 may be, for example, a glass rod, a large-core fiber, or another spacer that can be used to adjust the numerical aperture (NA) of a beam of light to the entrance of the optical-focusing component 303. By using glass-rod spacers of different lengths, the numerical aperture (NA) may be adjusted. Also, in some embodiments, the optical properties of the glass-rod spacer are adjustable, thereby allowing the NA to also be adjusted. And in some embodiments, an end face of the second light-guiding component 302 is fusion spliced to an end face of the first light-guiding component 301. Also, the y axis in FIG. 3A is aligned with a longitudinal axis of the first light-guiding component 301 or of the second light-guiding component 302. However, in some descriptions, the orientations of the x, y, and z axes are determined by the right-hand rule, in which the z axis is the axis of light propagation. Thus, if the z axis was the axis of light propagation, then the z axis in FIG. 3A would be aligned with the longitudinal axis of the first light-guiding component 301 or of the second light-guiding component 302.

In this embodiment, the optical-focusing component 303 is a ball lens that focuses a beam of light equally or nearly equally along orthogonal axes. Thus, the optical power of the ball lens may be equal or nearly equal on a first axis and on a second axis. Also, the optical-focusing component 303 may be attached to the second light-guiding component 302 or may be formed from an endface of the second light-guiding component 302, for example through a heating process.

The clear or mostly-clear sheath 330 (or window of the sheath 330) may introduce a negative optical power along a first axis (e.g., the x axis in FIG. 3A) and may introduce almost no optical power along a second axis (e.g., the y axis in FIG. 3A).

The ACBS 306 has a reflective surface 306a, which is a surface with a mirror finish. The reflective surface 306a also introduces an optical power (e.g., a negative optical power on a first axis, a positive optical power on a second axis) to compensate for the optical power of the sheath 330. For example, in some embodiments, the reflective surface 306a of the ACBS 306 has a positive optical power on a first axis (e.g., the x axis in FIG. 3A) that counteracts the effect of the sheath's negative optical power on the first axis and the ACBS 306 may have a cylindrical curvature that introduces a positive optical power on the first axis. Also, the optical-focusing component 303 may be designed to have an equal optical power on the first axis and on a second axis, and the equal optical power may be the same as or nearly the same as a desired total optical power.

For example, in some embodiments, the optical-focusing component 303 can be described by $P_x=P_y=P_{Desired}$ (where $P_x$ is the power on the x axis, $P_y$ is the power on the y axis, and $P_{Desired}$ is the desired power), the ACBS 306 can be described by $P_x$=Positive P (where P is an optical power) and $P_y$=0, and the sheath 330 can be described by $P_x$=Negative P and $P_y$=0. Note that this notation assumes that the z axis is the axis of light propagation both before and after the reflection from the ACBS 306 (for example as illustrated in FIGS. 5A-5B and 6A-6B), which eliminates the need to describe the axis change in FIG. 3A that is caused by the reflection of the ACBS 306.

Additionally, in some embodiments, the ACBS 306 has a cylindrical curvature that introduces a negative optical power on a second axis (e.g., the y axis in FIG. 3A) that matches the effect of the sheath's negative optical power on a first axis (e.g., the x axis in FIG. 3A). The optical-focusing component 303 may have an optical power that is equal on a first axis and a second axis and that is larger than the desired optical power such that the total optical power with the introduced negative optical powers from the ACBS 306 and the sheath 330 leads to the desired optical power.

For example, in some embodiments, the optical-focusing component 303 can be described by $P_x=P_y>P_{Desired}$, the ACBS 306 can be described by $P_x$=0 and $P_y$=Negative P, and the sheath 330 can be described by $P_x$=Negative P and $P_y$=0. Again, note that this notation assumes that the z axis is the axis of light propagation both before and after the reflection from the ACBS 306 (for example as illustrated in FIGS. 5A-5B and 6A-6B), which eliminates the need to describe the axis change in FIG. 3A that is caused by the reflection of the ACBS 306.

Also, the components of the optical-imaging device 39 can be selected to suit a particular environment. Some embodiments of the optical-imaging device 39 are specially configured for use in an air environment, and some embodiments of the optical-imaging device 39 are specially configured for a liquid environment. The liquids that compose the liquid environment may include, for example, saline, dextran, water, or a combination of liquids. The optical-focusing component 303, the ACBS 306, and the sheath 330 may be selected according to the refractive index of the environment in which the optical-imaging device 39 will be used.

Furthermore, some embodiments of the optical probe 300 are configured to transmit and emit beams of light in more than one wavelength. For example, some embodiments that are configured for multimodal optical coherence tomography emit one beam that has a wavelength that is suitable for OCT and emit another beam that has a wavelength that is suitable for fluorescence imaging. The sizes of the members of the optical probe 300 and the arrangement of the members of the optical probe 300 may be configured to produce a desired beam width and a desired working distance.

Some embodiments of the optical probe 300 are configured for a multimodality system that simultaneously performs OCT imaging using light with a wavelength of 1.31 um and fluorescence mapping using light with a wavelength of 0.633 um. Depending on the specification of the imaging, it may be critical to focus the OCT wavelength, which can provide structural information, at a designed optimal working distance to provide lateral resolution, while the fluorescence wavelength is focused slightly off from the optimal working distance of the OCT imaging, thereby allowing the fluorescence wavelength to have a larger beam size with a lower lateral resolution at the optimal working distance of the OCT imaging.

For example, in coronary arteries, the diameters of the arteries of interest are often about 2 to 4 mm. Assuming that the optical probe 300 is located at the center of the artery, the radius of the artery corresponds to the working distance, and is 1 to 2 mm from the optical axis of the optical probe 300.

OCT and fluorescence wavelengths both penetrate the vessel, so, in some embodiments, the focus position or the working distance is optimal at 1 to 3 mm. Within these working distances, the focus may be different between the two modalities. Some embodiments of the optical probe 300 (e.g., for coronary-artery measurement) have focal distances or working distances that are within 2 mm of each other. Some embodiments have larger differences in the focal distances or working distances, for example embodiments that are used for larger blood vessels (e.g., peripheral arteries), corresponding to the blood vessel's diameter and the desired working distance.

The optimization of the focal point may be accomplished by using the refractive indices for the two wavelengths and solving the optimization problem. When optimizing, it may be efficient to add another material, with a different combination of refractive indices for the two wavelengths, by splitting one or more optical components or by adding a spacer.

Also, some embodiments of the optical probe 300 are configured for other modalities, such as near-infrared spectroscopy, in addition to or in alternative to OCT and fluorescence imaging.

Figure 3B:
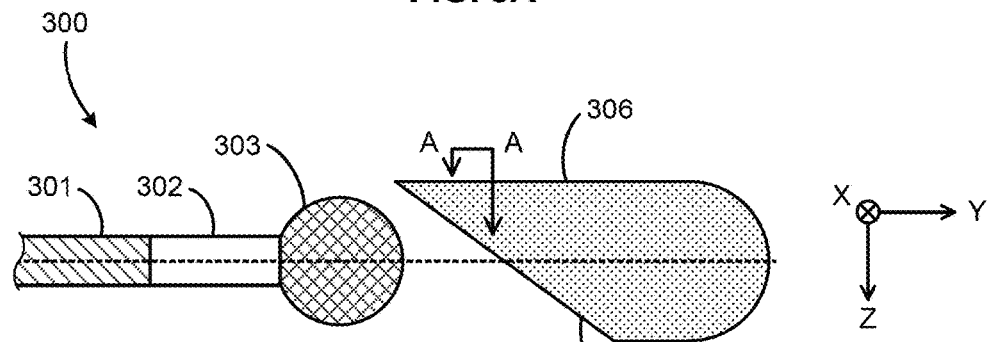
FIG. 3B illustrates an example embodiment of an optical probe.
Figure 3C:
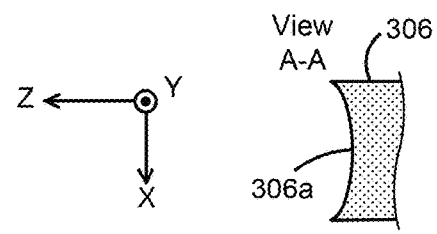
FIG. 3C illustrates an example embodiment of a reflective surface of an astigmatism-correction and beam-steering component (ACBS).

FIG. 3B illustrates an example embodiment of an optical probe 300. The optical probe 300 includes a first light-guiding component 301, a second light-guiding component 302, an optical-focusing component 303, and an ACBS 306. The ACBS 306 includes a reflective surface 306a. In this embodiment, the reflective surface 306a is a concave or a mostly-concave surface that introduces a positive optical power along a first axis (the x axis in FIG. 3B). FIG. 3C illustrates the reflective surface 306a from the perspective of line A-A. As shown in FIG. 3C, the reflective surface 306a is concave or mostly concave.

Figure 4:
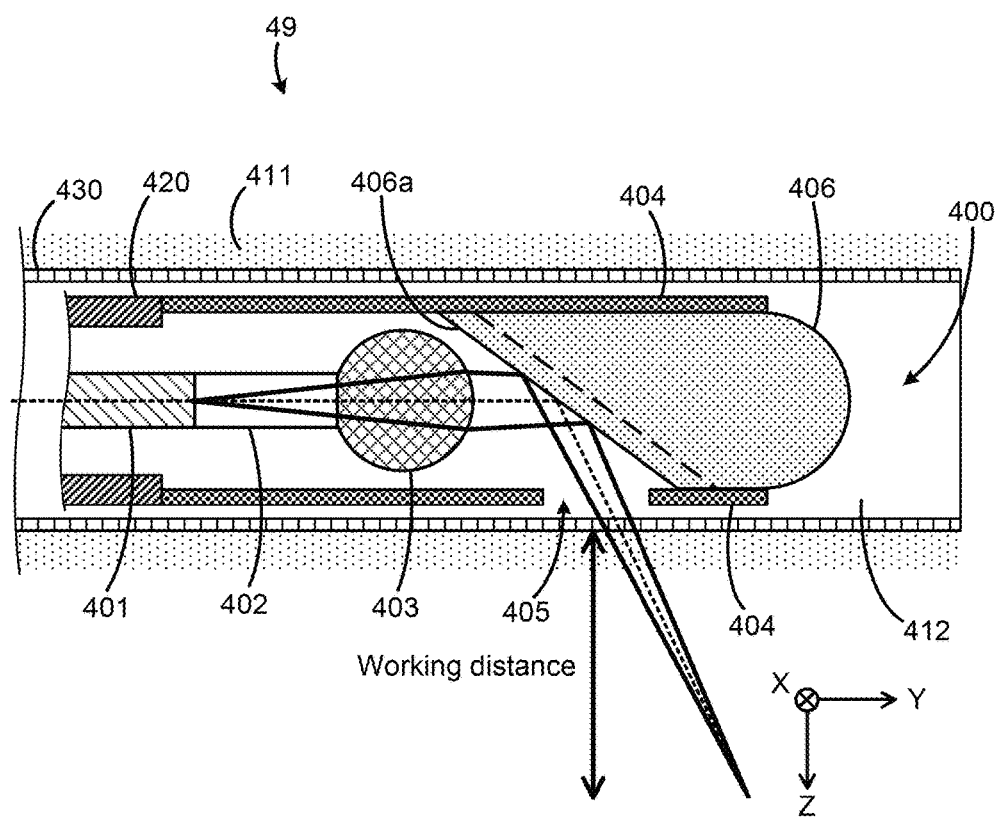
FIG. 4 illustrates a partially-cutaway view of an example embodiment of an optical-imaging device that includes an optical probe, a drive cable, and a sheath.

FIG. 4 illustrates a partially-cutaway view of an example embodiment of an optical-imaging device 49 that includes an optical probe 400, a drive cable 420, and a sheath 430. The optical probe 400 includes a first light-guiding component 401, a second light-guiding component 402, an optical-focusing component 403, a protector 404, and an ACBS 406. The drive cable 420 and the protector 404 may be attached to each other (e.g., welded together). Also, the optical probe 400 may be attached to the drive cable 420, for example by adhesives. And one or more other members of the optical probe 400 may be attached to the protector 404, for example by adhesives. The optical probe 400 is able to freely rotate inside the sheath 430.

In this embodiment, a light beam with a center wavelength of 1.3 μm is delivered from a light source (e.g., the light source 101 in FIG. 1) through the first light-guiding component 401, which is an optical fiber (e.g., a Corning SMF28ULTRA fiber). After exiting the first light-guiding component 401, the light beam diverges through the second light-guiding component 402, which is a glass-rod spacer that may be made of fused silica. Also, the second light-guiding component 402 may have a diameter (e.g., a diameter of 125 μm) that matches the outer diameter of the first light-guiding component 401. Additionally, in some embodiments, the length along the y axis of the second light-guiding component 402 is approximately 300 μm.

After the light beam has diverged in the second light-guiding component 402, the light beam is converged equally or nearly equally along both a first axis and a second axis by an optical-focusing component 403, which is a ball lens in this embodiment (ball lens 403). The diameter of the ball lens 403 is approximately 320 μm in some embodiments. Also, in some embodiments, the exit aperture of the ball lens 403 is anti-reflection coated to reduce back reflection.

The converging light beam then propagates through an inner medium 412, which is air in this example, and is reflected by the reflective surface 406a of the ACBS 406. The ACBS 406 may have different optical powers ($P_x, P_y$) along different axes. For example, assuming that the z axis is the axis of light propagation, $P_y$ may be approximately zero, and $P_x$ may be positive, such as in embodiments where the reflective surface 406a is a concave-cylindrical shape (e.g., FIG. 3C).

The spacing between the ball lens 403 and the ACBS 406 may operate to adjust and fine tune the optical power on one axis to adequately compensate for the astigmatism caused by the sheath 430. In some embodiments, the spacing is 50 to 350 μm. And the tip of the ACBS 406 may be chipped off in order to minimize the spacing between the ACBS 406 and the ball lens 403.

The length of the ACBS component 406 along the longitudinal axis of the optical probe 400 can be selected for ease of manufacturing and assembly. In some embodiments, the diameter of the ACBS 406 matches or nearly matches (to within a tolerance) the internal diameter of the protector 404. The angle θ of the reflecting surface 406a relative to the longitudinal axis of the optical probe 400 may be between 30° and 60°. In some embodiments, the angle is between 53° and 58°, which may reduce back reflections from the sheath 430 and may point the beam slightly forward.

After a light beam reflects off the reflective surface 406a, the light beam passes through an opening of the protector 404 (e.g., a hole 405 in a radio-opaque metallic protector 404) and then through the sheath 430. In some embodiments, the sheath 430 has an inner diameter of 600 μm, an outer diameter of 800 μm, and a refractive index of 1.50. Optically, the sheath 430 has a negative optical power along a first axis (e.g., the x axis in FIG. 4) and an optical power of zero along a second axis that is orthogonal to the first axis (e.g., the y axis in FIG. 4).

After traveling through the sheath 430, the light beam travels through the outer medium 411, which is a contrast agent in this embodiment. In some embodiments, the contrast agent has a refractive index of 1.45 and surrounds the outside of the sheath 430.

The combination of the ball lens 403, the ACBS 406, and the sheath 430 may cause the light beam to focus in both the x axis and the y axis at a desired working distance, for example at 2.1 mm from the sheath's outer surface, which is also 2.5 mm from the longitudinal axis along the center of the optical probe 400 when the outer diameter of the sheath 430 is 800 μm.

Furthermore, in some embodiments the ACBS 406 has two axes that have non-negligible optical powers that make a beam of light converge at the same working distance. Accordingly, some embodiments of the ACBS 406 have more than one axis on which the optical power is not negligible.

In some embodiments, a ball lens 403 that has a symmetric optical power and an ACBS 406 that does not have any optical power cause the beam in a direction along a second axis (the y axis) to focus at a working distance of about 2.1 mm from the outer surface of the sheath 430. However, because the ACBS 406 does not compensate for the astigmatism of the sheath 430, the beam in a direction along a first axis (the x axis) may focus at working distance of about 4.2 mm from the outer surface of the sheath 430 due the negative power of the sheath 430 along the first axis. Thus, the astigmatism from the sheath 430 causes the beam to focus on the x axis direction at a different working distance (4.2 mm) than the working distance on they axis (2.1 mm).

Figure 5A:
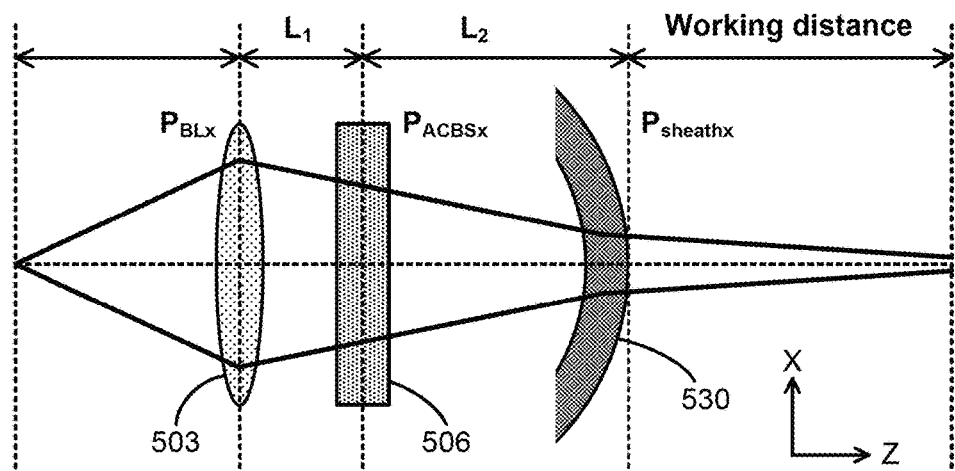
FIGS. 5A and 5B are conceptual illustrations that show the focusing of a beam of light on two orthogonal planes.
Figure 5B:
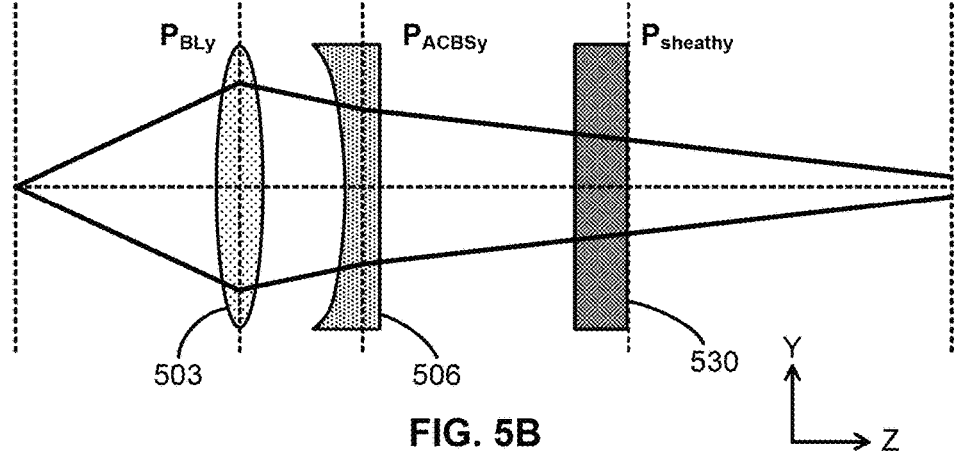

FIGS. 5A and 5B are conceptual illustrations that show the focusing of a beam of light on two orthogonal planes. FIGS. 5A and 5B are simplified illustrations that show only three members of an optical system: an optical-focusing component 503, an ACBS 506, and a sheath 530. FIG. 5A shows the three members in the x-z plane, and FIG. 5B shows the three members in the y-z plane. As shown by FIGS. 5A and 5B, the optical power of the sheath 530 on the x axis is different from the optical power of the sheath 530 on the y axis. Also, the optical power of the ACBS 506 on the x axis is different from the optical power of the ACBS 506 on the y axis. In this example, the optical power of the ACBS on the x axis is zero or approximately zero, and the optical power of the ACBS on the y axis is negative. The optical power of the ACBS 506 compensates for the optical power of the sheath 530 so that the working distance on the x-z plane is the same or nearly the same (i.e., to within a tolerance) as the working distance on the y-z plane.

The optical system focuses the light at a working distance (W). The combined optical powers of the three members may be described by equation (1) and equation (2):

$$P_{y'} = P_{BL_y} P_{ACBS_y} - P_{BL_y} P_{ACBS_y} L_1, \text{ and}$$

$$P_y = P_{y'} + P_{sheath_y} - P_{y'} P_{sheath_y} L_2; \tag{1}$$

$$P_{x'} = P_{BL_x} + P_{ACBS_x} - P_{BL_x} P_{ACBS_x} L_1, \text{ and}$$

$$P_x = P_{x'} + P_{sheath_x} - P_{x'} P_{sheath_x} L_2; \tag{2}$$

where ($P_y$) is the total optical power along the y axis, where ($P_x$) is the total optical power along the x axis, where ($P_{BL_y}$) is the optical power of the optical-focusing component 503 along the y axis, where ($P_{BL_x}$) is the optical power of the optical-focusing component 503 along the x axis, where $P_{ACBS_y}$) is the optical power of the ACBS 506 along the y axis, where ($P_{ACBS_x}$) is the optical power of the ACBS 506 along the x axis where ($P_{sheath_y}$) is the optical power of the sheath 530 along the y axis, where ($P_{sheath_x}$) is the optical power of the sheath 530 along the x axis, where ($L_1$) is an optical distance between the optical-focusing component 503 and the ACBS 506, and where ($L_2$) is an optical distance between the ACBS 506 and the sheath 530.

Also, the optical distance between the optical-focusing component 503 and the sheath 530 can be divided into a plurality of distances with respective refractive indices ($n_j$), as described by the following:

$$L_i = \sum_{j=k}^{m} L_j n_j; i = 1, 2; \tag{3}$$

where i=1 ($L_1$) is the distance between the optical-focusing component 503 and the sheath 530, and where i=2 ($L_2$) is the distance between the ACBS 506 and the sheath 530.

Note that equations (1), (2), and (3) may be a simplification because, after the first two optical elements, the optical length ($L_2$) may no longer be accurate to describe the final optical power once the third element is introduced. An optical-design-optimization tool may be used to adequately determine the properties of the optical components to reach a target total optical power that is mostly equal along both a first axis and a second axis.

In some embodiments, $P_{sheath_x}$ may be approximated with zero, and in some embodiments $P_{ACBS_y}$ may be approximated with zero. The optical powers may then be optimized such that $P_y \cong P_x$, which produces the following:

$$P_y \cong P_x + P_{sheath_x} - P_x P_{sheath_x} L_2. \qquad (4)$$

In some embodiments, the optical power of the sheath on the y axis $P_{sheath_y}$) can be approximated using the thin-lens equation, as described in equation (5) below, in which R is the inner diameter of the sheath 530 and ΔR is the thickness of the sheath 530:

$$P_{sheath_y} \cong \frac{-1}{R} + \frac{-1}{R + \Delta R} \cong \frac{-\Delta R}{R(R + \Delta R)}. \qquad (5)$$

In some embodiments, the ACBS 506 compensates for the asymmetric distortion of the sheath 530 such that the beam of light focuses at about the same working distance on the x axis and on the y axis, which produces a small spot size.

Figures 6A, 6B:
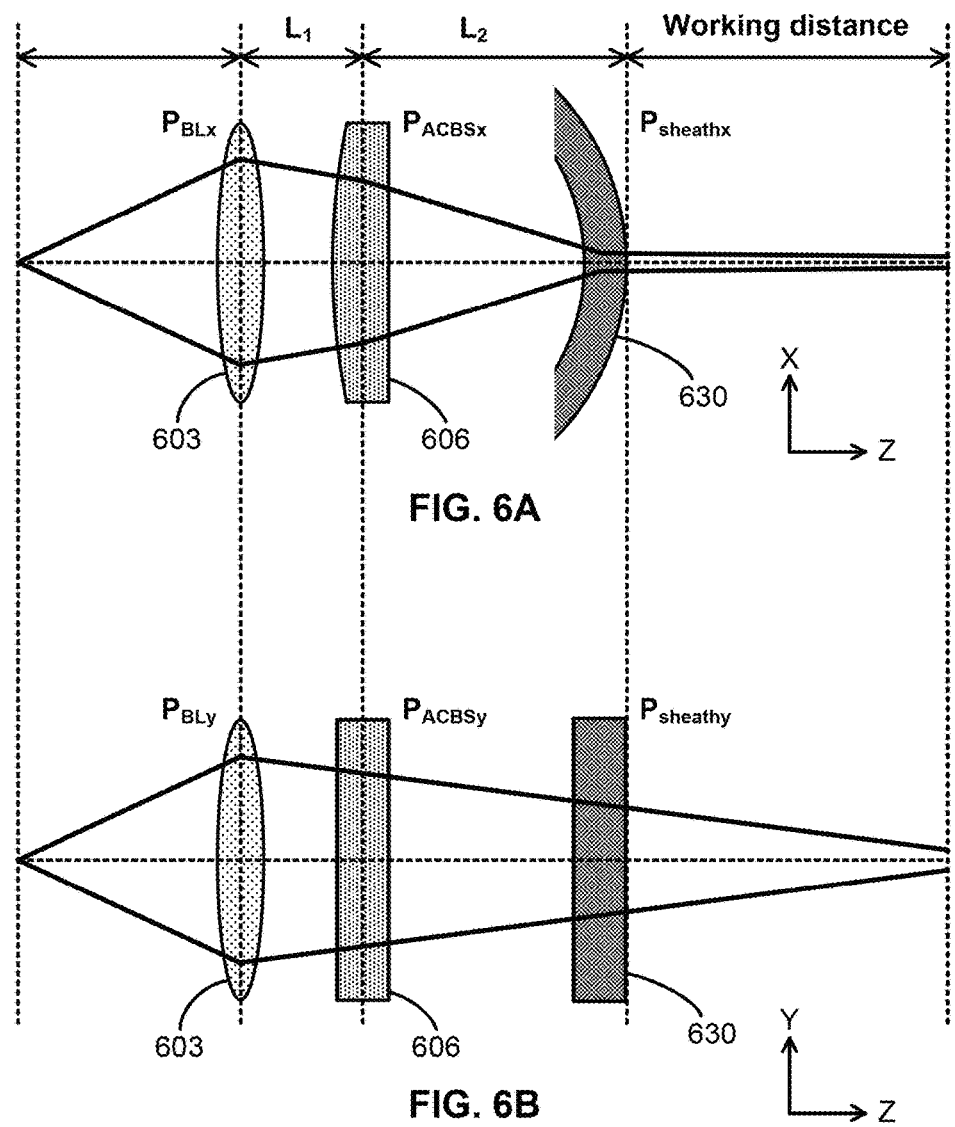
FIGS. 6A and 6B are conceptual illustrations that show the focusing of a beam of light on two orthogonal planes.

FIGS. 6A and 6B are conceptual illustrations that show the focusing of a beam of light on two orthogonal planes. FIGS. 6A and 6B are simplified illustrations that show only three members of an optical system: an optical-focusing component 603, an ACBS 606, and a sheath 630. FIG. 6A shows the three members on the x-z plane, and FIG. 6B shows the three members on the y-z plane. As shown by FIGS. 6A and 6B, the optical power of the sheath 630 on the x axis is different from the optical power of the sheath 630 on the y axis. Also, the optical power of the ACBS 606 on the x axis is different from the optical power of the ACBS 606 on the y axis. In this example, the optical power of the ACBS on the y axis is zero or approximately zero, and the optical power of the ACBS on the x axis is positive. The optical power of the ACBS 606 compensates for the optical power of the sheath 630 so that the working distance on the x-z plane is the same or nearly the same as the working distance on the y-z plane.

Figure 7:
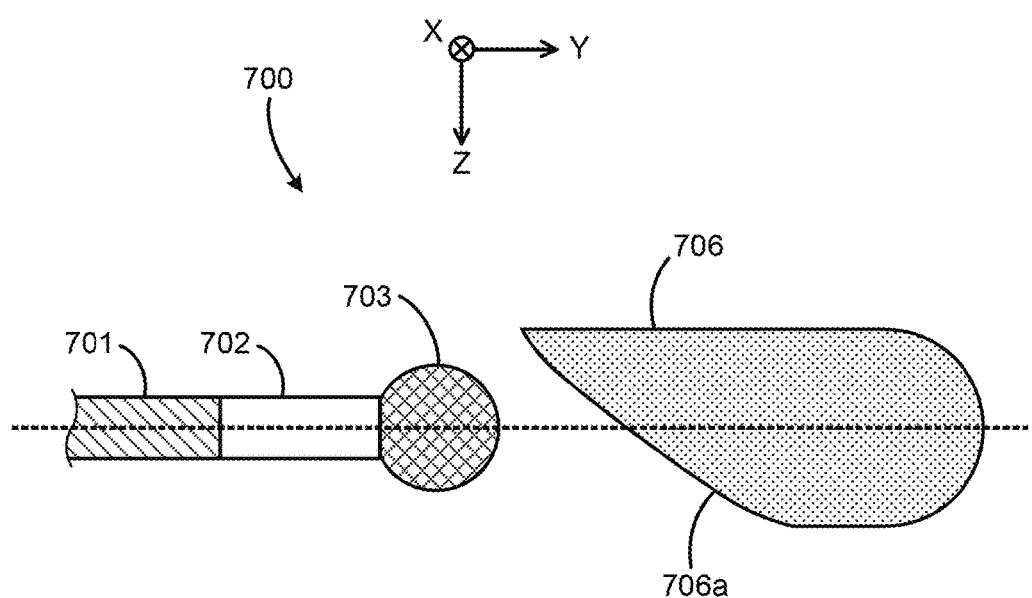
FIG. 7 illustrates an example embodiment of an optical probe.

FIG. 7 illustrates an example embodiment of an optical probe. The optical probe 700 includes a first light-guiding component 701, a second light-guiding component 702, an optical-focusing component 703, and an ACBS 706. The ACBS 706 includes a reflective surface 706a. In this embodiment, the reflective surface 706a is convex and introduces a negative optical power along an axis.

Figure 8A:
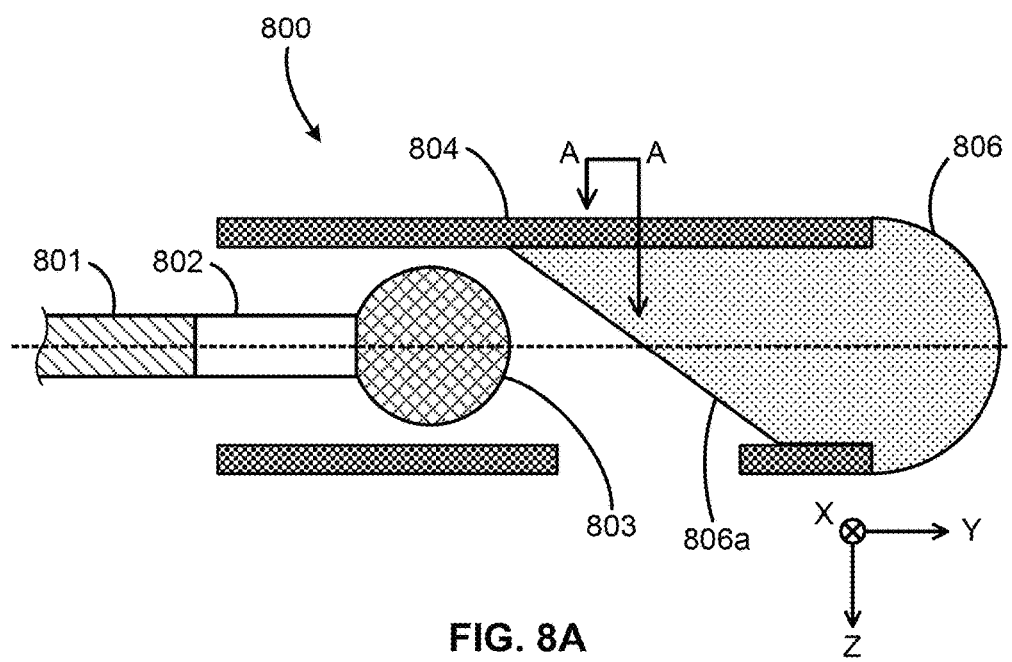
FIG. 8A illustrates an example embodiment of an optical probe.

FIG. 8A illustrates an example embodiment of an optical probe. The optical probe 800 includes a first light-guiding component 801, a second light-guiding component 802, an optical-focusing component 803, a protector 804, and an ACBS 806. The ACBS 806 includes a reflective surface 806a. In this embodiment, the ACBS 806 is shaped in such a way that it acts as a plug for the protector 804. This may make the distal tip of the optical probe 800 atraumatic for safety considerations, for example by reducing the effects of drill-through when there is a kink in the sheath and the probe is advanced into the kink.

Figure 8B:
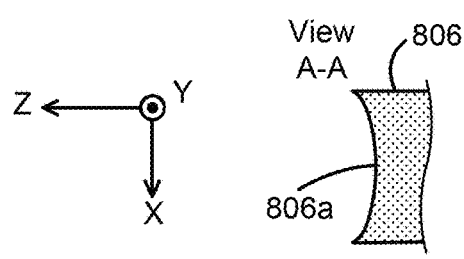
FIG. 8B illustrates an example embodiment of a reflective surface of an ACBS.

Also, in this embodiment, the reflective surface 806a is a concave or mostly-concave surface that introduces a positive optical power along a first axis (the x axis in this embodiment). FIG. 8B illustrates the reflective surface 806a from the perspective of line A-A. As shown in FIG. 8B, the reflective surface 806a is concave or mostly concave.

Figure 9:
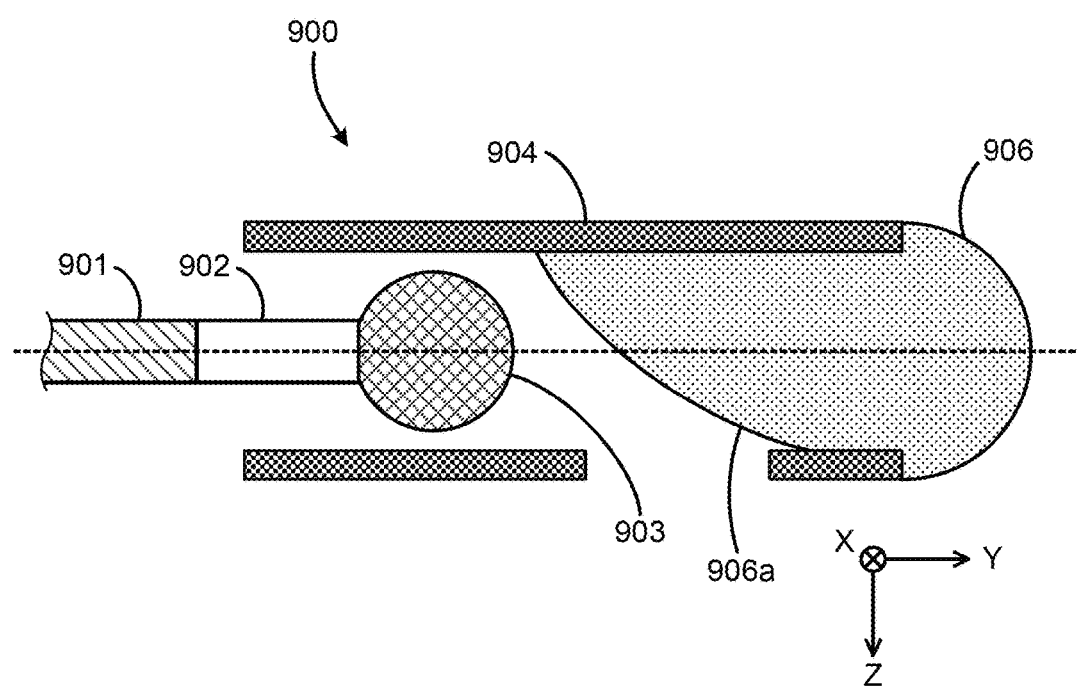
FIG. 9 illustrates an example embodiment of an optical probe.

FIG. 9 illustrates an example embodiment of an optical probe. The optical probe 900 includes a first light-guiding component 901, a second light-guiding component 902, an optical-focusing component 903, a protector 904, and an ACBS 906. The ACBS 906 includes a reflective surface 906a. In this embodiment, the ACBS 906 is shaped in such a way that it acts as a plug for the protector 904. Also, in this embodiment, the reflective surface 906a is a convex or mostly convex surface that introduces a negative optical power along a first axis (the y axis in this embodiment).

Figure 10A:
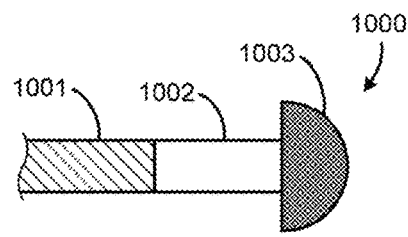
FIGS. 10A-10G illustrate example embodiments of optical probes.

FIGS. 10A-10G illustrate example embodiments of optical probes. In FIG. 10A, the optical probe 1000 includes a first light-guiding component 1001, a second light-guiding component 1002, and an optical-focusing component 1003. The optical-focusing component 1003 is a half-ball lens. In this embodiment, the outer diameter of the second light-guiding component 1002 matches the outer diameter of the first light-guiding component 1001.

Figure 10B:
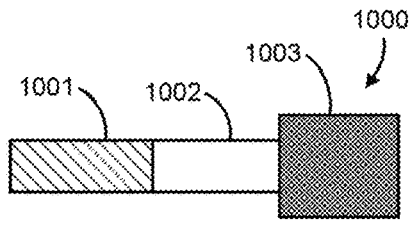

In FIG. 10B, the optical probe 1000 includes a first light-guiding component 1001, a second light-guiding component 1002, and an optical-focusing component 1003. The optical-focusing component 1003 is a gradient index (GRIN) lens. In this embodiment, the outer diameter of the second light-guiding component 1002 matches the outer diameter of the first light-guiding component 1001.

Figure 10C:
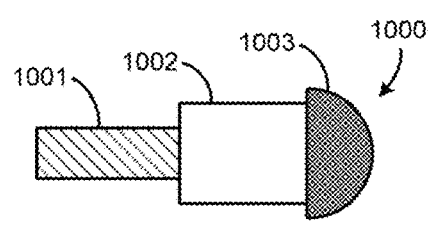

In FIG. 10C, the optical probe 1000 includes a first light-guiding component 1001, a second light-guiding component 1002, and an optical-focusing component 1003. The optical-focusing component 1003 is a half-ball lens. In this embodiment, the outer diameter of the second light-guiding component 1002 is larger than the outer diameter of the first light-guiding component 1001. Also, the outer diameter of the second light-guiding component 1002 or the outer diameter of the optical-focusing component 1003 may match the inner diameter of a protector.

Figure 10D:
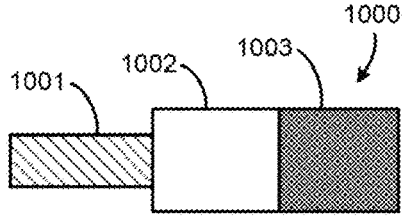

In FIG. 10D, the optical probe 1000 includes a first light-guiding component 1001, a second light-guiding component 1002, and an optical-focusing component 1003. The optical-focusing component 1003 is a GRIN lens. In this embodiment, the outer diameter of the second light-guiding component 1002 is larger than the outer diameter of the first light-guiding component 1001 and is equal to the outer diameter of the optical-focusing component 1003. Also, the outer diameter of the second light-guiding component 1002 and the outer diameter of the optical-focusing component 1003 may match the inner diameter of a protector.

Figure 10E:
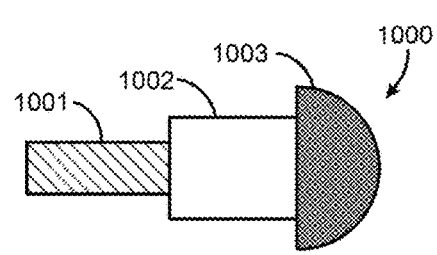

In FIG. 10E, the optical probe 1000 includes a first light-guiding component 1001, a second light-guiding component 1002, and an optical-focusing component 1003. The optical-focusing component 1003 is a half-ball lens. In this embodiment, the outer diameter of the second light-guiding component 1002 is larger than the outer diameter of the first light-guiding component 1001. Also, the outer diameter of the second light-guiding component 1002 or the outer diameter of the optical-focusing component 1003 may match the inner diameter of a protector.

Figure 10F:
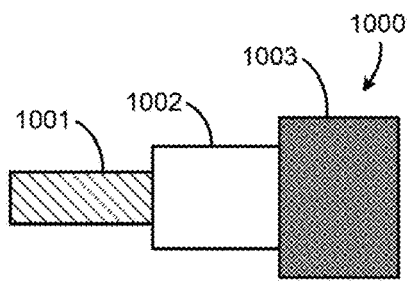

In FIG. 10F, the optical probe 1000 includes a first light-guiding component 1001, a second light-guiding component 1002, and an optical-focusing component 1003. The optical-focusing component 1003 is a GRIN lens. In this embodiment, the outer diameter of the second light-guiding component 1002 is larger than the outer diameter of the first light-guiding component 1001 and is smaller than the outer diameter of the optical-focusing component 1003. Also, the outer diameter of the second light-guiding component 1002 or the outer diameter of the optical-focusing component 1003 may match the inner diameter of a protector.

Figure 10G:
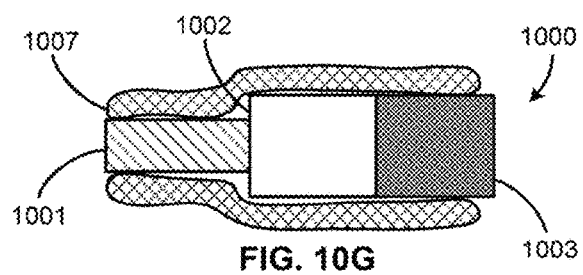

In FIG. 10G, the optical probe 1000 includes a first light-guiding component 1001, a second light-guiding component 1002, and an optical-focusing component 1003. The optical-focusing component 1003 is a GRIN lens. In this embodiment, the outer diameter of the second light-guiding component 1002 is larger than the outer diameter of the first light-guiding component 1001 and is equal to the outer diameter of the optical-focusing component 1003. In this embodiment, a sleeve 1007 surrounds portions of the first light-guiding component 1001, the second light-guiding component 1002, and the optical-focusing component 1003. The sleeve 1007 may be heat-shrink tubing and may be made from a low-refractive-index material, which may prevent the sleeve 1007 from affecting light propagation in the first light-guiding component 1001 (e.g., when the first light-guiding component 1001 is a double-clad fiber).

The scope of the claims is not limited to the above-described embodiments and includes various modifications and equivalent arrangements. Also, as used herein, the conjunction "or" generally refers to an inclusive "or," although "or" may refer to an exclusive "or" if expressly indicated or if the context indicates that the "or" must be an exclusive "or."

The invention claimed is:

1. A device comprising:
   a first light-guiding component;
   a second light-guiding component;
   a lens;
   an optical-correction component that has a reflecting surface that faces the lens;
   a protector that surrounds at least part of the lens and at least a part of the optical-correction component; and
   a sheath, in which at least a portion of the lens, at least a portion of the protector, and at least a portion of the optical-correction component are disposed,
   wherein the sheath causes an astigmatism,
   wherein the reflecting surface has an optical power on a first axis of two orthogonal axes and the optical power on the first axis compensates for the astigmatism,
   wherein the reflecting surface has a negligible optical power on a second axis of the two orthogonal axes,
   wherein the reflecting surface is configured to reflect light from the lens and redirect the reflected light through the sheath, and
   wherein the optical-correction component does not directly contact the lens.

2. The device of claim 1, wherein the lens is one of a gradient-index lens, a GI-fiber lens, a ball lens, and a half-ball lens.

3. The device of claim 1,
   wherein the sheath further includes at least a portion of the first light-guiding optical component and at least a portion of the second light-guiding optical component therein.

4. The device of claim 1, wherein one or more of:
   an outer diameter of the optical-correction component is equal to or approximately equal to an inner diameter of the protector; and
   an outer diameter of the optical-correction component is equal to or approximately equal to an inner diameter of the protector such that the optical-correction component operates to define, plug or cap part of a wall or boundary of the protector.

5. The device of claim 1, wherein an outer diameter of the lens is equal to or approximately equal to an inner diameter of the protector.

6. The device of claim 1, wherein the protector has a window,
   wherein the optical-correction component and the window are arranged such that the reflected light travels through the window.

7. The device of claim 1, wherein the sheath has a negative optical power in the first axis.

8. The device of claim 7, wherein the optical power of the optical-correction component on the first axis is a positive optical power.

9. The device of claim 1, wherein the sheath has a negative optical power in the second axis.

10. The device of claim 9, wherein the optical power of the optical-correction component on the first axis is a negative optical power.

11. The device of claim 1, wherein the sheath operates to cover and protect at least the portion of the lens, at least the portion of the protector, and at least the portion of the optical-correction component in the event that the sheath and the components therein are in vivo.

12. The device of claim 1, wherein one or more of:
   the optical-correction component includes a cylindrical curvature that makes the optical power on the first axis a positive optical power;
   the sheath has inner and outer surfaces that are curved in a sagittal direction of the device;
   the inner and outer surfaces of the sheath are mostly flat in a tangential direction of the device;
   the optical power at the outer surface is not as strong as the optical power at the inner surface due to a radius of the curvature of the outer surface being larger than a radius of the curvature of the inner surface; and
   the reflecting surface has: (i) a negative optical power on the first axis and a positive optical power on the second axis, or (ii) a positive optical power on the first axis and a negative optical power on the second axis.

13. A device comprising:
   a light-guiding component;
   an optical-focusing component;
   an optical-correction component that has a reflecting surface that faces the optical-focusing component, wherein the reflecting surface has an optical power on a first axis and is configured to reflect light from the optical-focusing component and redirect the reflected light;
   a protector that surrounds at least part of the optical-focusing component and at least a part of the optical-correction component; and
   a sheath, in which at least a portion of the optical-focusing component, at least a portion of the protector, and at least a portion of the optical-correction component are disposed.

14. The device of claim 13, wherein the optical power is a positive optical power.

15. The device of claim 13, wherein the optical power is a negative optical power.

16. The device of claim 13, wherein the reflecting surface has a negligible optical power on a second axis that is orthogonal to the first axis.

17. The device of claim 13, wherein the optical-correction component does not contact the optical-focusing component.

18. A device comprising:
   a first light-guiding component;

a second light-guiding component;

a lens;

a protector that surrounds at least part of the lens and that includes a window; and an optical-correction component that has a reflecting surface that faces the lens, wherein the reflecting surface has an optical power and is configured to reflect light from the lens and redirect the reflected light through the window of the protector, and wherein the optical-correction component operates to define, plug or cap a part of a wall or boundary of the protector.

19. The device of claim 18, wherein the optical-correction component includes a distal end that has a hemispherical shape.

20. The device of claim 19, wherein a diameter of the hemispherical shape matches an outer diameter of the protector.

21. The device of claim 18, wherein the optical power is a positive optical power.

22. The device of claim 18, wherein the optical power is a negative optical power.

23. The device of claim 18, wherein the first light-guiding component, the second light-guiding component, the lens, and the optical-correction component are configured to transmit a first beam of light for optical coherence tomography and are configured to transmit a second beam of light for fluorescence imaging.

24. The device of claim 18, wherein the optical-correction component corrects an astigmatism in a wavelength of light for optical-coherence-tomography imaging.

25. The device of claim 18, wherein the optical-correction component corrects an astigmatism in a wavelength of light for fluorescence excitation.

26. The device of claim 18, wherein the optical-correction component corrects an astigmatism in a wavelength of light for optical-coherence-tomography imaging and wherein the optical-correction component corrects an astigmatism in a wavelength of light for fluorescence excitation such that a mean focal distance of the wavelength of light for optical-coherence-tomography imaging is within 2 mm of a mean focal distance of the wavelength of light for fluorescence excitation.

* * * * *